(12) United States Patent
Vrba et al.

(10) Patent No.: US 6,254,609 B1
(45) Date of Patent: Jul. 3, 2001

(54) SELF-EXPANDING STENT DELIVERY SYSTEM WITH TWO SHEATHS

(75) Inventors: Anthony C. Vrba, Maple Grove; David J. Sogard, Edina, both of MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/228,097

(22) Filed: Jan. 11, 1999

(51) Int. Cl.[7] .................................................. A61F 2/00
(52) U.S. Cl. ............................................................ 606/108
(58) Field of Search .................................. 606/108, 198, 606/194; 623/1.11, 1.12

(56) References Cited

U.S. PATENT DOCUMENTS

| | | |
|---|---|---|
| 4,732,152 | 3/1988 | Wallstèn et al. .................. 128/343 |
| 5,201,757 | 4/1993 | Heyn et al. ......................... 606/198 |
| 5,405,378 * | 4/1995 | Strecker . |
| 5,534,007 | 7/1996 | St. Germaine et al. ........... 606/108 |
| 5,591,226 * | 1/1997 | Trerotola et al. ............... 606/108 X |
| 5,593,412 * | 1/1997 | Martinez et al. .................. 606/108 |
| 5,702,364 | 12/1997 | Euteneuer et al. .................. 604/96 |
| 5,733,267 | 3/1998 | Del Toro ............................. 604/280 |
| 5,735,859 | 4/1998 | Cottone .............................. 606/108 |
| 5,766,203 * | 6/1998 | Imran et al. .................... 606/108 X |
| 5,792,144 | 8/1998 | Fischell et al. .................... 606/108 |
| 5,800,517 | 9/1998 | Anderson et al. ..................... 623/1 |
| 5,810,837 | 9/1998 | Hofmann et al. .................. 606/108 |

FOREIGN PATENT DOCUMENTS

| | | |
|---|---|---|
| 0 368 523 A2 | 5/1990 | (EP) . |
| 0 696 447 A2 | 2/1996 | (EP) . |
| 96/32078 | 10/1996 | (WO) . |
| 98/12988 | 4/1998 | (WO) . |
| 98/39056 | 9/1998 | (WO) . |

* cited by examiner

*Primary Examiner*—Jeffrey A. Smith
(74) *Attorney, Agent, or Firm*—Vidas, Arrett & Steinkraus

(57) ABSTRACT

A medical device delivery system is disclosed which has a distal inner sheath and a distal outer sheath covering a medical device mounting region and any medical device mounted thereon. The outer sheath is designed to retain the medical device for lengthy periods of time while the inner sheath is designed to retain the sheath for shorter periods of time.

29 Claims, 7 Drawing Sheets

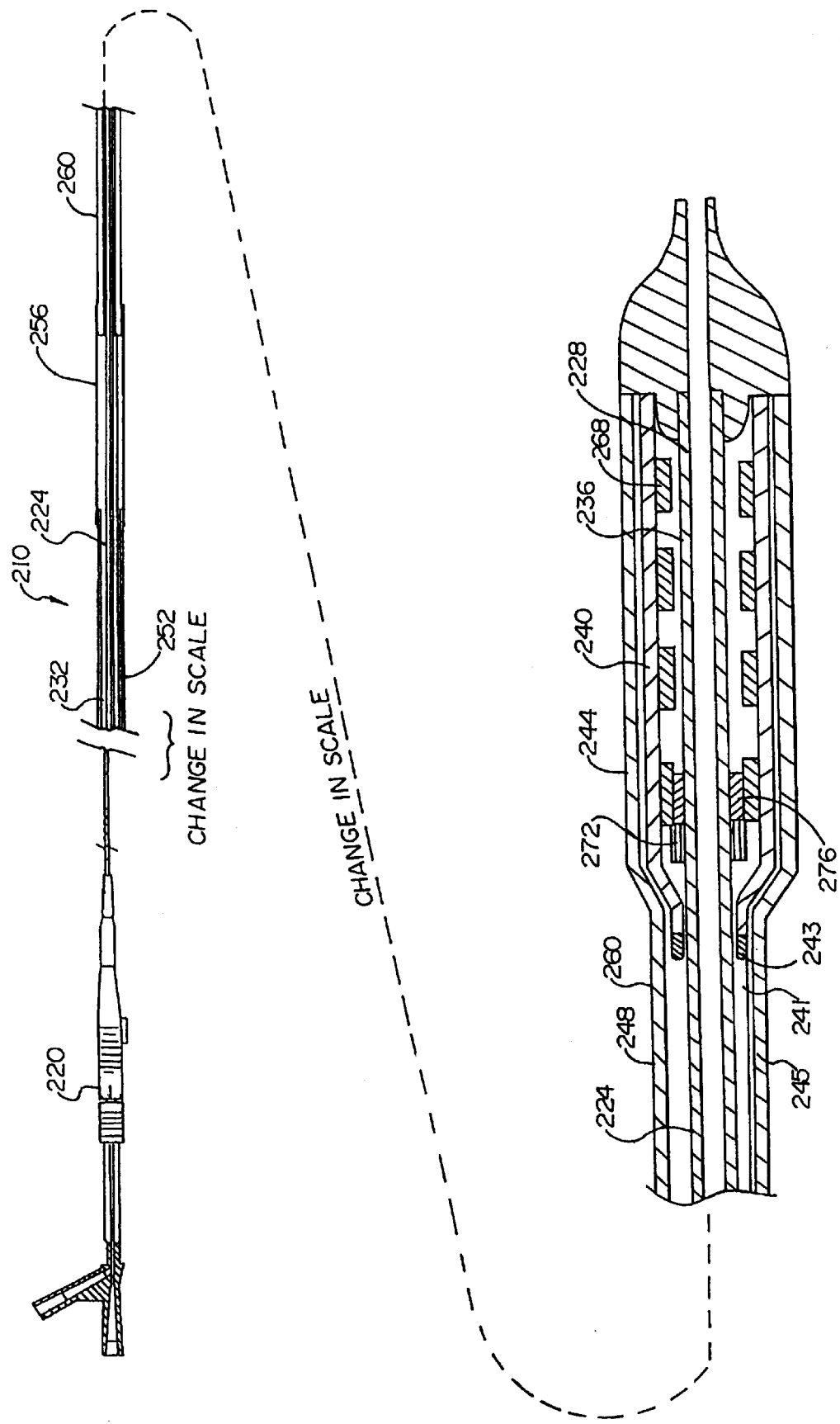

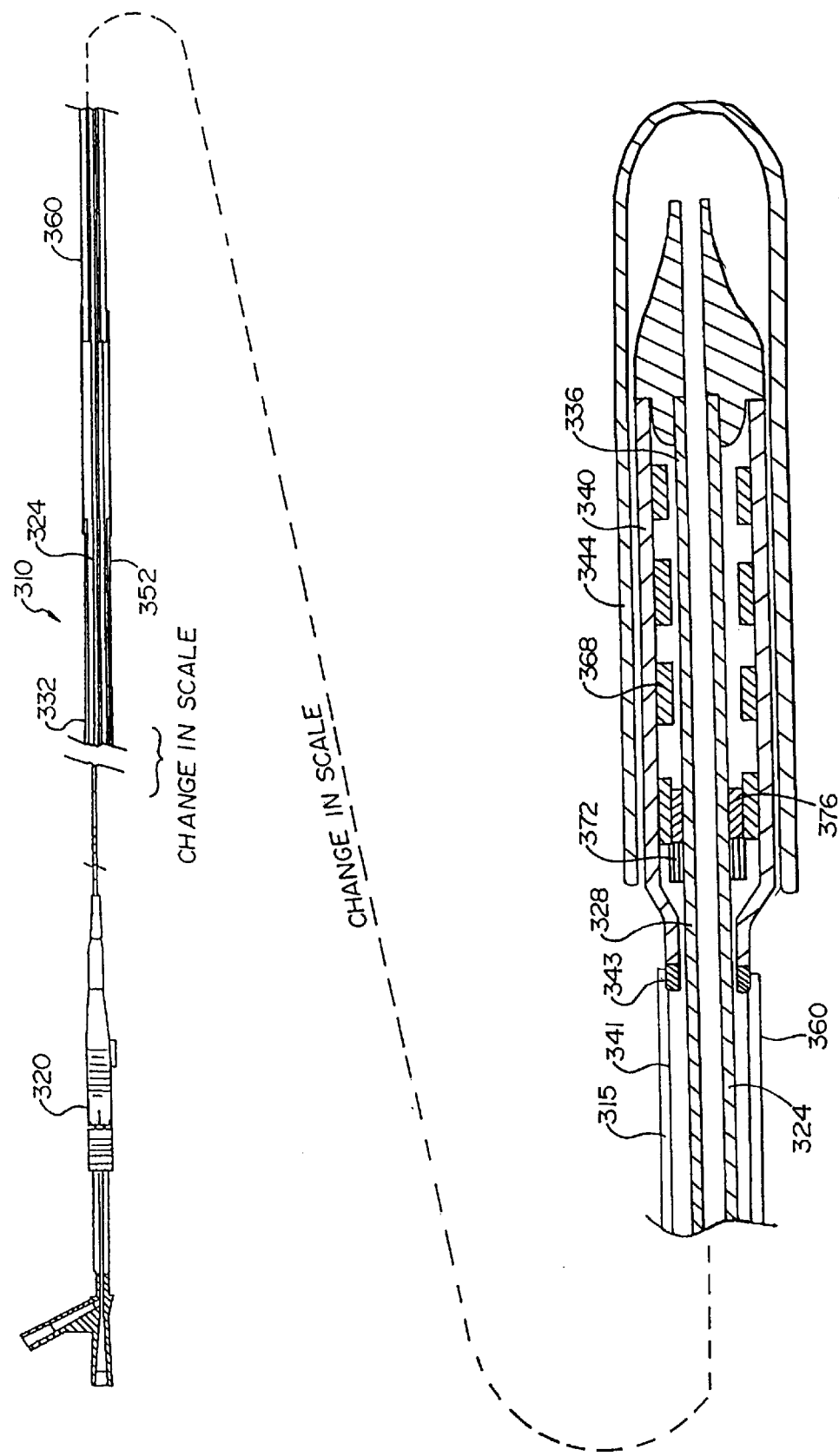

SELF-EXPANDING STENT DELIVERY SYSTEM WITH TWO SHEATHS

FIELD OF THE INVENTION

This invention relates to a stent delivery catheter system, such as the kind used in percutaneous transluminal coronary angioplasty (PTCA) procedures. More particularly, it relates to a stent delivery catheter employing two retractable sheaths which may be retracted to release a self-expanding stent, a balloon assisted expandable stent or a balloon expandable stent.

BACKGROUND OF THE INVENTION

In typical PTCA procedures, a guiding catheter is percutaneously introduced into the cardiovascular system of a patient and advanced through the aorta until the distal end is in the ostium of the desired coronary artery. Using fluoroscopy, a guide wire is then advanced through the guiding catheter and across the site to be treated in the coronary artery. An over the wire (OTW) balloon catheter is advanced over the guide wire to the treatment site. The balloon is then expanded to reopen the artery. The OTW catheter may have a guide wire lumen which is as long as the catheter or it may be a rapid exchange catheter wherein the guide wire lumen is substantially shorter than the catheter. Alternatively, a fixed wire balloon catheter could be used. This device features a guide wire which is affixed to the catheter and cannot be removed.

To help prevent arterial closure, repair dissection, or prevent restenosis, a physician can implant an intravascular prosthesis, or a stent, for maintaining vascular patency inside the artery at the lesion. The stent may either be a self-expanding stent, a balloon assisted expandable stent or a balloon expandable stent. For the latter type, the stent is often delivered on a balloon and the balloon is used to the expand the stent. The self-expanding stents may be made of shape memory materials such as nitinol or constructed of regular metals but of a design which exhibits self expansion characteristics.

In certain known stent delivery catheters, a stent and an optional balloon are positioned at the distal end of the catheter, around a core lumen. The stent and balloon are held down and covered by a sheath or sleeve. When the distal portion is in its desired location of the targeted vessel the sheath or sleeve is retracted to expose the stent. After the sheath is removed, the stent is free to self-expand or be expanded with a balloon.

In a coronary stent deployment system which utilizes a retractable sheath one problem which is encountered is the interaction of the sheath and the stent upon retraction of the sheath. Typically, as the sheath slides off of the stent, the stent is subjected to potential marring by the sheath. While this problem can be minimized by making the sheath of soft materials, such materials are often unsuitable for use with a self-expanding stent where prolonged storage results in creep deformation of the inner sheath.

It is desirable to provide a medical device delivery system which provides a protective, non-marring inner sheath for the medical device and is capable of retaining the medical device for brief periods of time and which further has an additional outer sheath over the inner sheath which is capable of retaining the medical device for lengthy periods of time, thereby allowing the device to have a suitable shelf life.

SUMMARY OF THE INVENTION

The present invention provides a medical device delivery system in which two sheaths, an inner sheath and an outer sheath, cover a medical device mounted on the distal end of the medical device delivery system. In its various embodiments, the invention contemplates a delivery system in which the inner sheath is either a tear away sheath or a retractable sheath and the outer sheath is either a retractable sheath or a pull away sheath.

In accordance with the present invention, the outer sheath is desirably constructed to be more creep resistant than the inner sheath. The outer sheath may be made of a material having a higher hoop strength than the inner material. The inner material should be capable of retaining the medical device in place on the delivery system for at least a short period of time before it either is retracted or opens due to material failure. The outer sheath should be capable of retaining the medical device for longer periods of time so that the device may have a reasonable shelf life.

To this end, the invention provides a medical device delivery system comprising a manifold at the proximal end of the delivery system. Extending distally from the manifold is an inner tube. At the distal end of the inner tube is a medical device mounting region for concentrically mounting a medical device thereon. Covering the medical device mounting region, at least in part, is a distal inner sheath attached to the inner tube at the distal region of the inner tube. The distal inner sheath is concentrically disposed about the inner tube. The medical device delivery system also comprises a distal outer sheath, concentrically disposed about the inner tube. At least a portion of the distal outer sheath is disposed about at least a portion of inner sheath.

In one embodiment of the invention, the distal inner sheath is a tear away sheath and the distal outer sheath is retractable by means of an outer sheath retraction device. The outer sheath retraction device extends in a distal direction from the manifold. The distal outer sheath extends from the distal end of the retraction device.

In another embodiment of the invention, the distal inner sheath is retractable by means of an inner sheath retraction device. The inner sheath retraction device extends in a distal direction from the manifold. The distal inner sheath extends from the distal end of the inner sheath retraction device. Similarly, the outer sheath is retractable by means of an outer sheath retraction device. The outer sheath retraction device extends in a distal direction from the manifold. The distal outer sheath extends from the distal end of the outer sheath retraction device.

In another embodiment of the invention, the distal inner sheath is retractable by means of an inner sheath retraction device. The inner sheath retraction device extends in a distal direction from the manifold. The distal inner sheath extends from the distal end of the inner sheath retraction device. The distal outer sheath contacts the inner sheath, and extends proximally from the distal region of the inner tube. The distal outer sheath is removed prior to insertion of the device in the body.

In all of the embodiments, the delivery system may further comprise the medical device mounted on the medical device mounting region. Among the contemplated medical device for use with this system are stents and grafts. Desirably, the stent will be self-expanding or a balloon assisted expandable stent.

BRIEF DESCRIPTION OF THE FIGURES

FIG. 4 shows a longitudinal cross-sectional view of an embodiment of the inventive medical device delivery system.

FIG. 5 shows a longitudinal cross-sectional view of an embodiment of the inventive medical device delivery system.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

The present invention provides a medical device delivery system in which the medical device is contained and/or surrounded and/or protected by both an inner sheath and an outer sheath.

In several of the embodiments, the inner sheath is a tear away sheath. The presence of a tear away inner sheath protects the medical device from being marred upon the sliding removal of the outer sheath. After the outer sheath is removed, the inner tear away sheath, no longer contained by the outer sheath, opens as a result of the expanding force of the self-expanding, balloon assisted or balloon expandable medical device.

Figure 1:
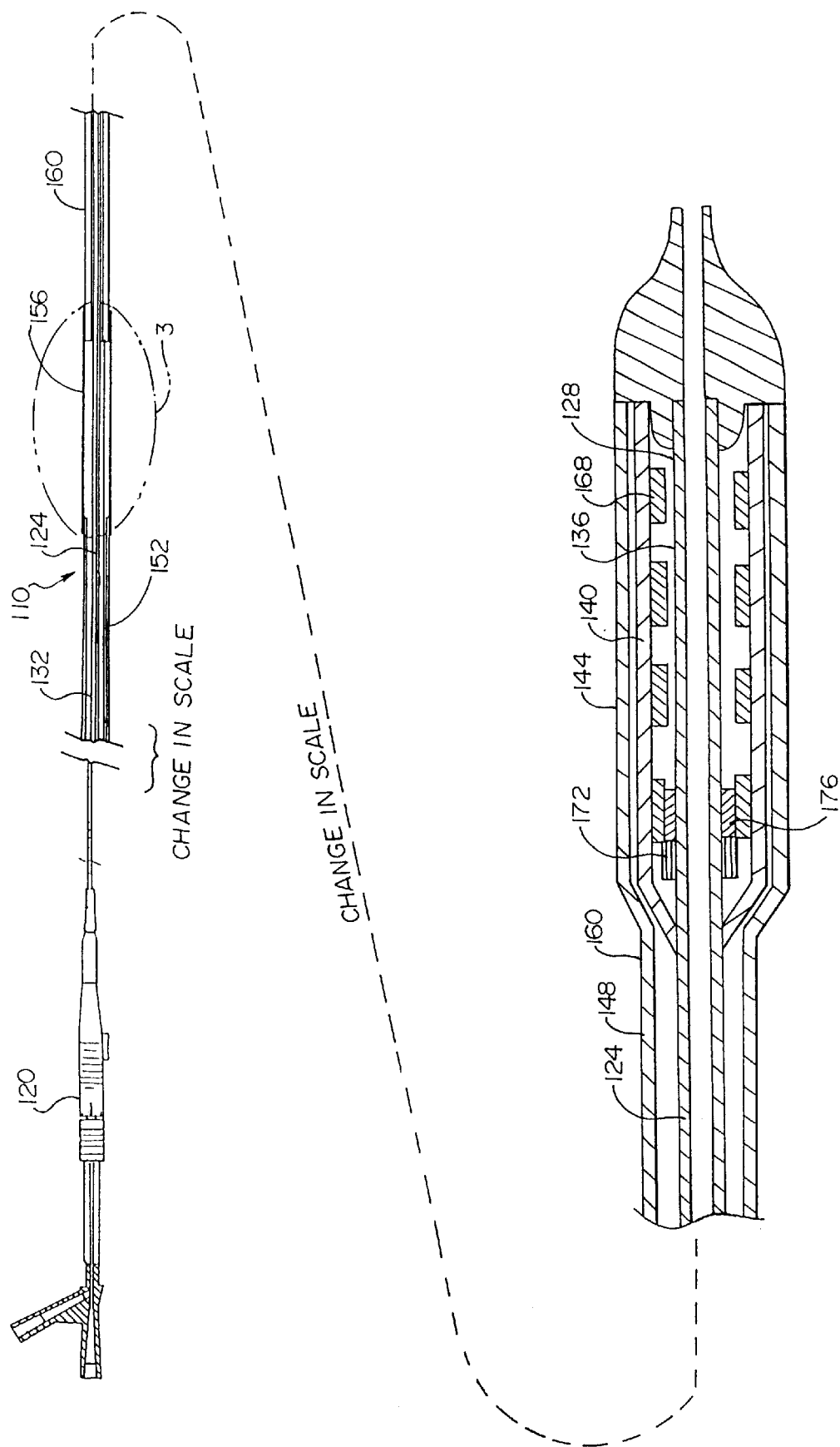
FIG. 1 shows a longitudinal cross-sectional view of an embodiment of the inventive medical device delivery system.
Figure 2:
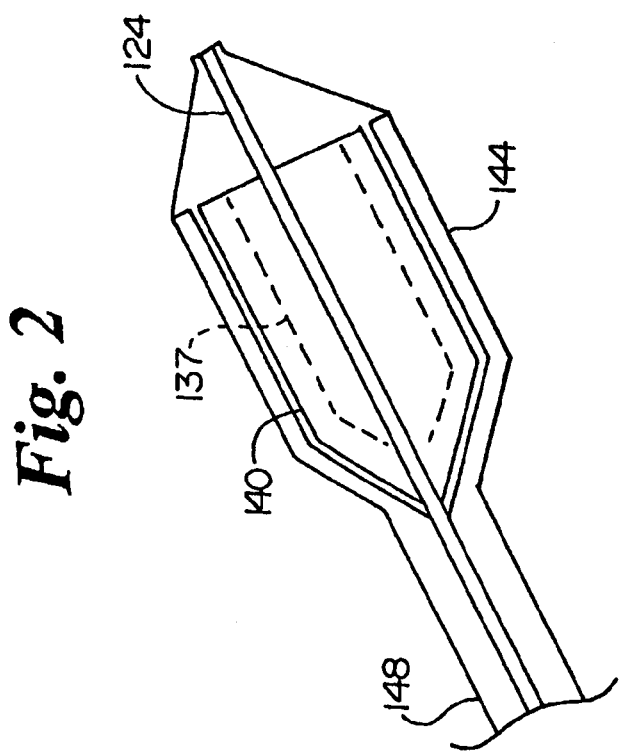
FIG. 2 shows a partial cut-away perspective view of the distal end of the embodiment of FIG. 1.

Turning to the figures, FIG. 1 shows one embodiment of the inventive medical device delivery system generally at 110. The medical device delivery system 110 has a proximal end and a distal end and comprises a manifold 120 located at the proximal end of delivery system 110. Extending in a distal direction from manifold 120 is an inner tube 124 having a distal region 128 and a proximal region 132. At the distal region of inner tube 124 is a medical device mounting region 136 for concentrically mounting a medical device thereon. Delivery system 110 further comprises a distal inner sheath 140 attached to inner tube 124 at distal region 128. Distal inner sheath 140 is concentrically disposed about inner tube 124 and covers at least a portion, desirably a substantial portion and more desirably the entirety of medical device mounting region 136 to retain a medical device about the medical device mounting region. Inner sheath 140 is fixedly attached to the medical device delivery system and desirably is mounted to the inner tube. As shown in FIG. 2, distal inner sheath 140 is a perforated 137 or scored tear away sheath. A distal outer sheath 144 is concentrically disposed about inner tube 124 and at least a portion of distal outer sheath 144 is disposed about at least a portion of distal inner sheath 140. The device further comprises an outer sheath retraction device 148 which extends in a distal direction from manifold 120. Distal outer sheath 144 is seen to extend from the distal end of outer sheath retraction device 148.

Figure 3:
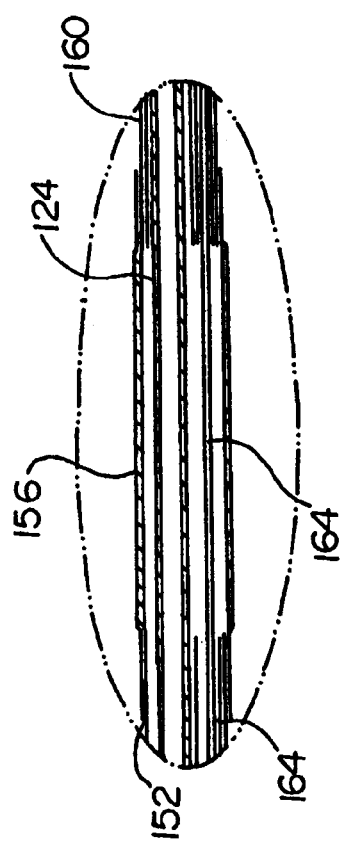
FIG. 3 shows an enlarged view of region 3 of the medical device delivery system of FIG. 1.

Although there are a variety of outer sheath retraction devices that may be used in the practice of the invention, as shown in FIGS. 1 and 3, a preferred outer sheath retraction device 148 comprises a proximal outer tube 152, a collapsible sheath 156 extending from the distal end of proximal outer tube 152 and a distal outer tube 160. The proximal end of distal outer tube 160 extends from the distal end of the collapsible sheath 156. A slidable pull wire 164 extends from manifold 120 to distal outer sheath 144. In use, the distal end of retraction device 148 moves in a proximal direction upon sliding pull wire 164 proximally thereby retracting distal outer sheath 144. Tear away inner sheath 140 may then open as a result of the force of the expansion of the expandable medical device. Because the tear away inner sheath is fixedly attached to the medical device delivery system, the tear away inner sheath is withdrawn from the body of the medical device delivery system is withdrawn.

The stent delivery system may, optionally, further comprise a medical device mounted on the medical device mounting region 136. While a variety of medical devices are contemplated, in the embodiment shown in FIGS. 1 and 2, the medical device is a self-expanding stent 168.

In another embodiment of the inventions, as shown in FIG. 4, the delivery system, shown generally at 210, comprises a manifold 220, an inner tube 224 having a distal region 228, a proximal region 232 and a medical device mounting region 236 for concentrically mounting a medical device thereon as in the previous embodiment. Similarly, as in the previous embodiment, delivery system 210 further comprises a distal inner sheath 240. Distal inner sheath 240 is concentrically disposed about inner tube 224 and covers at least a portion of medical device mounting region 236. Unlike in the previous embodiment, delivery system 210 further comprises a inner sheath retraction device 241 having a distal end and a proximal end. Inner sheath retraction device 241, consists of pull collar 243 mounted on proximal end of distal end of inner sheath 240 and a pull wire 245 extending distally from manifold 220 to pull collar 243.

As in the previous embodiment, a distal outer sheath 244 is concentrically disposed about inner tube 224. At least a portion of distal outer sheath 244 is disposed about at least a portion of distal inner sheath 240. Also, the device comprises an outer sheath retraction device 248 comprising a proximal outer tube 252, a collapsible sheath 256 and a distal outer tube 260 as described for the embodiment of FIGS. 1–3. The collapsible sheath section of the medical device delivery system is similar to that shown in FIG. 3, differing only in the presence of an additional wire, corresponding to a slidable pull-wire operably associated with the inner sheath. Slidable wire 264 extends from manifold 220 to distal outer sheath 244 and in use, the outer sheath retraction device works in a manner identical to that described for the outer sheath retraction device described above. Alternatively, although not shown in FIG. 4, inner sheath 240 may also be retracted via a collapsible retraction device similar to retraction device 248 used to retract outer sheath 244.

Also shown is an optional medical device in the form of a self-expanding stent 268 mounted on the medical device mounting region 236.

In another embodiment, the invention comprises a medical device delivery system shown generally at 310 in FIG. 5. Medical device delivery system 310, as in the previous embodiments, comprises a manifold 320, an inner tube 324 having a distal region 328, a proximal region 332 and a medical device mounting region 336 for concentrically mounting a medical device thereon. Delivery system 310 further comprises a distal inner sheath 340. Distal inner sheath 340 is concentrically disposed about inner tube 324 and covers at least a portion of medical device mounting region 336. As in the embodiment of FIG. 4, delivery system 310 further comprises a inner sheath retraction device 341 having a distal end and a proximal end. Inner sheath retraction device 341, consists of pull collar 343 mounted on proximal end of distal end of inner sheath 340 and a pull wire 345 extending distally from manifold 320 to pull collar 343.

As in the previous embodiments, a distal outer sheath 344 (in sock form) is concentrically disposed about inner tube 324. At least a portion of distal outer sheath 344 is disposed concentrically about at least a portion of distal inner sheath 340. Unlike in any of the previous embodiments, distal outer sheath 344 extends proximally from the distal end of the inner tube and is removable by sliding the distal outer sheath in a distal direction. Distal outer sheath 344 is in contact with distal inner sheath 340. Mounted concentrically about the inner tube and carrying the pull wire is outer tube 360. Although distal outer sheath 344 is depicted in FIG. 5 as being closed at the distal end, it may optionally be open at the distal end. In use, distal outer sheath 344 is removed prior to insertion of the medical device delivery system into the body. A removable sheath such as that disclosed in U.S. Pat. No. 5,800,517 to Anderson et al., incorporated herein in its entirety by reference, may be used.

Also shown is an optional medical device in the form of a self-expanding stent 368 mounted on the medical device mounting region 336.

In another embodiment, not shown, the medical device delivery system is substantially similar to that shown in FIG. 5 differing only in that the retraction device for retracting the inner sheath is a collapsible sheath as shown in FIGS. 1 and 3.

In the various embodiments of the invention, suitable manifolds, as are known in the art, may be employed. In the embodiment containing two retractable sheaths, the manifold must be able to accommodate two retraction mechanism. In the other embodiments in which one retraction device is employed, the manifold must be able to accommodate one retraction device.

The inner tubes employed in the various embodiments may be made of suitable materials as are known in the art including. Preferably, the inner tubes are made of flexible, but incompressible construction such as a polymer encapsulated braid or coil. Such construction is known in the art. The braid/coil may be comprised of stainless steel encased in a polymer such as Polyimide with an inner layer of Teflon.

The pull collars attached to the retractable sheaths may suitably be ringshaped members made of stainless steel affixed to the interior of the retractable sheaths by an appropriate adhesive such as Loctite 4011, a cyanoacrylate. Desirably, the pull collar will be made of a radio-opaque material such as gold.

The outer sheath, desirably will be made of a material which has sufficient strength to contain a self-expanding stent in the stent's unexpanded configuration. It is desirable that the outer sheath be constructed so as to be creep resistant. It is also highly desirable that the inner sheath be constructed to be less creep resistant than the outer sheath.

Some of the benefits of the present invention may also be realized in a system wherein the outer sheath is made of a thicker material than the inner sheath.

Suitable materials for the outer sheath include polyimide, Pebax, polyethylene, Nylon, and metal for the embodiments in which the outer sheath is retractable via a retraction device extending to the manifold. Suitable materials for the sock-like distal outer sheath include polyimide, Pebax, polyethylene, Nylon, and metal. As for the distal inner sheath, suitable materials include PTFE, Pebax, polyurethane, polyethylene, and polyimide for the tear away embodiments and for the retractable distal inner sheath embodiments.

The invention also contemplates the use of porous materials for the inner and outer sheaths thereby allowing for the inflow of bodily fluids into the medical device mounting region. This can be helpful in priming the medical device by forcing out any air in the region of the medical device. Suitable porous materials include Suitable porous materials include expanded polytetrafluoroethylene (ePTFE), polyester and silicone. Desirably, the materials will have a pore size ranging from 0.01 mm to 5.0 mm.

Although the tear away sheath has been described as being mechanically released by the force of the expanding medical device, the invention also contemplates the use of a tear away sheath which is hydrolytically released. The sheath may be 'glued' shut via a bio-compatible water soluble material. The sheath may then be opened by supplying water thereto so as to dissolved the 'glue'. Optionally, the glue may be chosen such that it is stable in the presence of fluids at bodily temperatures by dissolves upon exposure to a fluid of slightly elevated temperature such as water at a temperature of 42° C. Alternatively, the sheath may be glued shut via a material which is releasable via actinic energy such as ultraviolet radiation or gamma radiation supplied thereto.

The distal inner and outer sheaths may be bonded to the inner tube and/or retraction devices by the use of suitable adhesives including Loctite 4011, a cyanoacrylate as well as methacrylate, or H.B. Fuller 3507, a urethane adhesive. Other suitable bonding methods include pressure welding, heat welding and laser welding.

The invention also contemplates the use of various lubricants on at least a portion of one or more of the inner and outer sheaths to facilitate the relative motion of the inner and outer sheaths upon retraction or removal of the outer sheath. As seen in FIG. 2, distal inner sheath 140 has an inner surface facing the inner tube and an outer surface 138 facing distal outer sheath 144. Similarly, distal outer sheath 144 has an inner surface 146 facing distal inner sheath 140 and an outer surface facing outward. A lubricant may applied to at least a portion of at least one of outer surface 138 of inner sheath 140 or inner surface 146 of outer sheath 144 so as to reduce frictional forces between the two sheathes. The lubricant may be applied selectively to the surfaces or, alternatively, may be applied to the entirety of the surfaces.

Although the inner surface and outer surface to which lubricants may be applied have been highlighted in FIG. 2, it is understood that the invention provides for the similar use of such lubricants on the outer surface of the inner sheath and the inner surface of the outer sheath in the other embodiments as well.

In all of the above embodiments, a lubricant may, optionally, be applied to at least a portion of the inner wall and/or outer wall. Suitable lubricants include silicones, PVP (polyvinyl pyrrolidone), PPO (polypropylene oxide) and PEO. Additionally, BioSlide™ coating produced by SciMed made be used as well. BioSlide™ is a hydrophilic, lubricious coating comprising polyethylene oxide and neopentyl glycol diacrylate polymerized in a solution of water and isopropyl alcohol in the presence of a photoinitiator such as azobisisobutronitrile.

Additional details of the design of embodiments of the inventive medical device delivery system which employ collapsible sheaths, in particular the portion of the device proximal to the inner sheath may be found in the various embodiments disclosed in U.S. Pat. No. 5,534,007 to St. Germain and Olson, incorporated herein in its entirety by reference.

In addition to the use of a collapsible sheath retraction device for retracting the outer sheath, the invention also contemplates the use of other suitable retraction means as are known in the art including slidably sealed retractable sheaths and midshaft seals as described in co-pending commonly assigned U.S. patent application Ser. No. 08/722,834 filed Sep. 27, 1996 now U.S. Pat. No. 5,772,669, and a continuation-in-part application Ser. No. 09/071,484 filed May 1, 1998 now U.S. Pat. No. 5,957930. The entire contents of both applications are hereby incorporated in their entirety by reference. Other contemplated retraction means include sheaths activated directly by pull-collars as described in U.S patent application Ser. No. 09/071,484 filed May 27, 1998, now U.S. Pat. No. 5,7957,930, and screw-like retraction devices as described in U.S. Pat. No. 5,201,757 to Heyn et al. all of which are incorporated herein in their entirety by reference.

Figure 6:
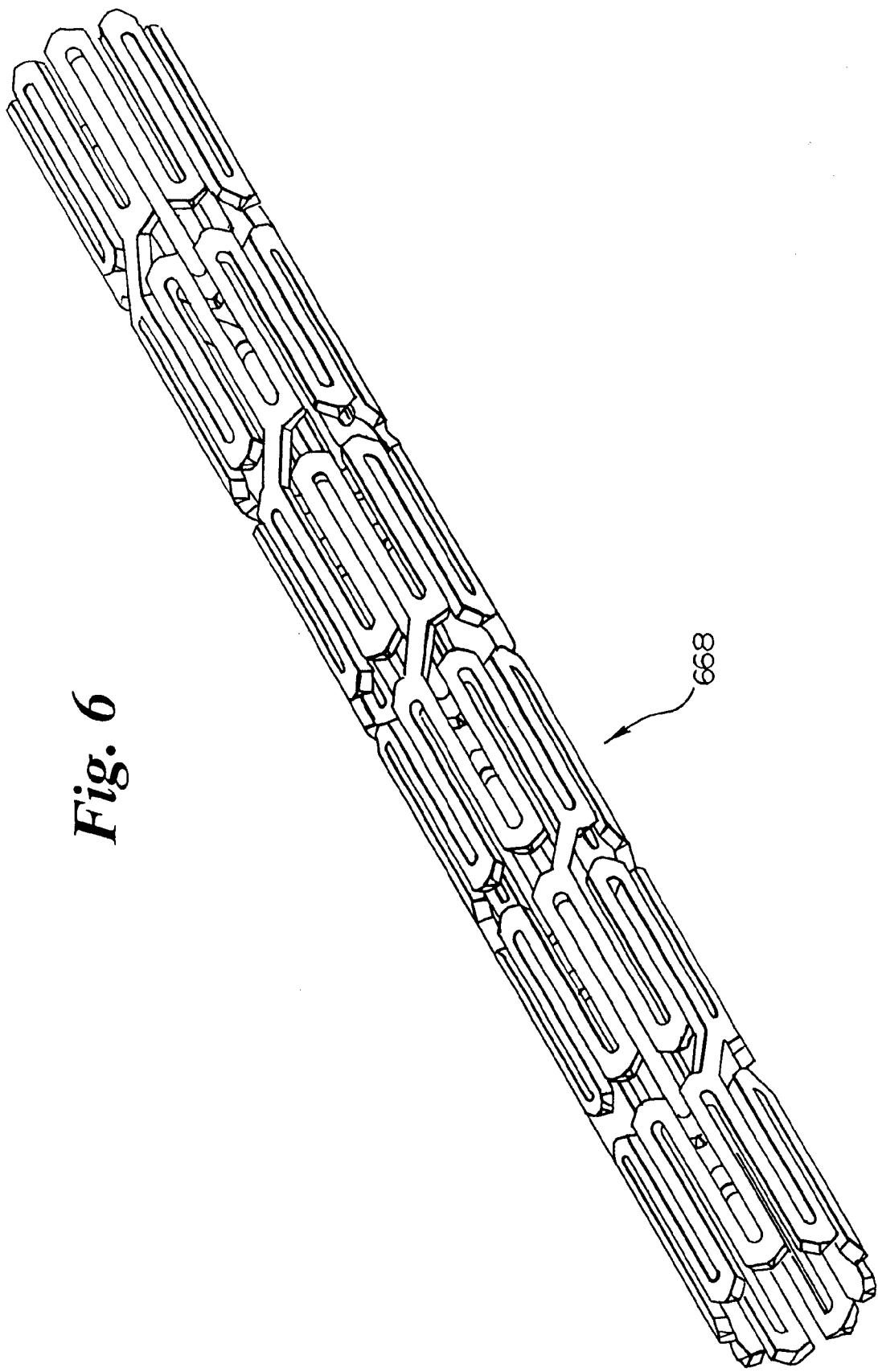
FIG. 6 shows a perspective view of a stent for use with the inventive medical device delivery system.
Figure 7:
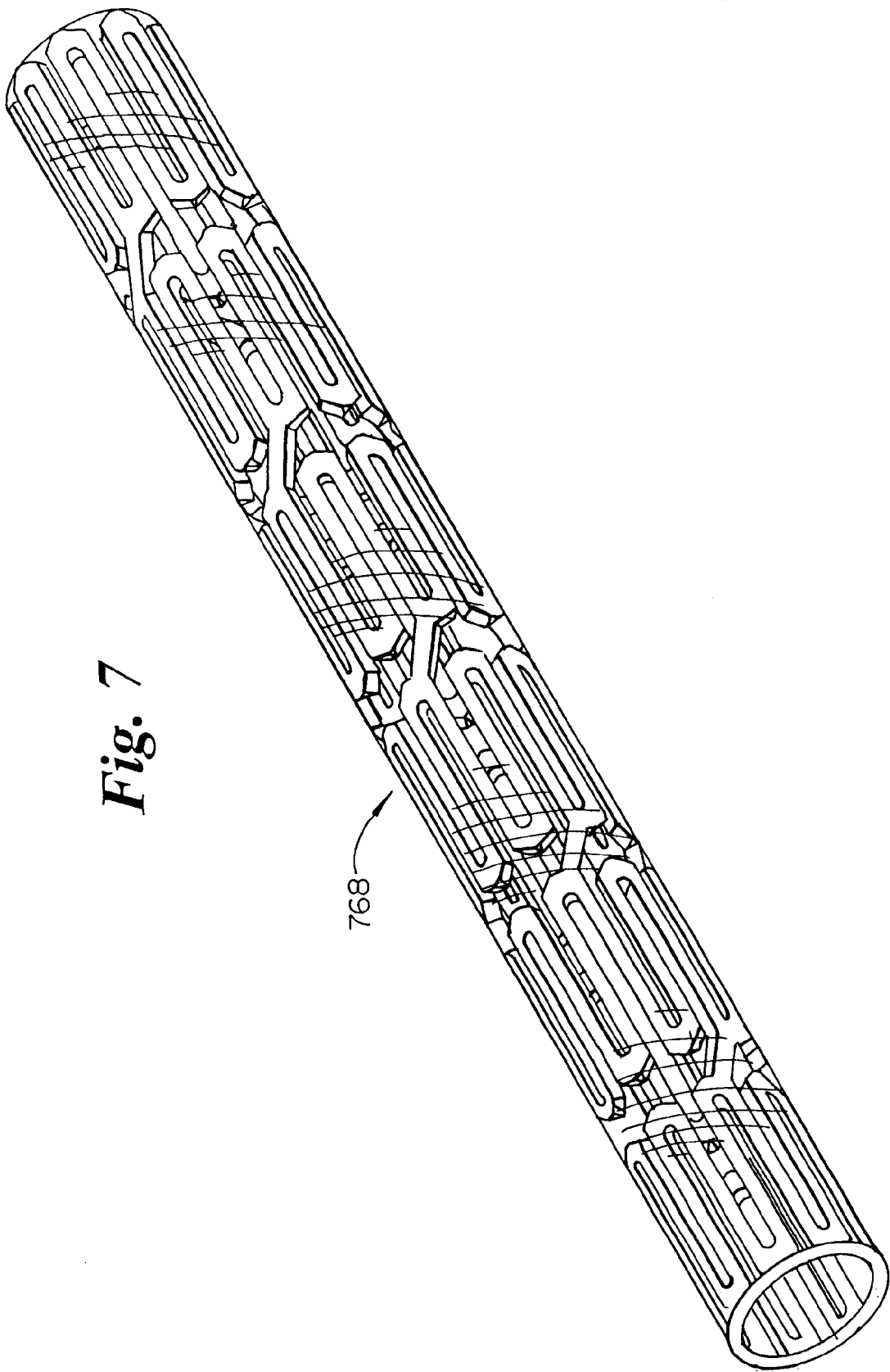
FIG. 7 shows a perspective view of a graft for use with the inventive medical device delivery system.
Figure 8:
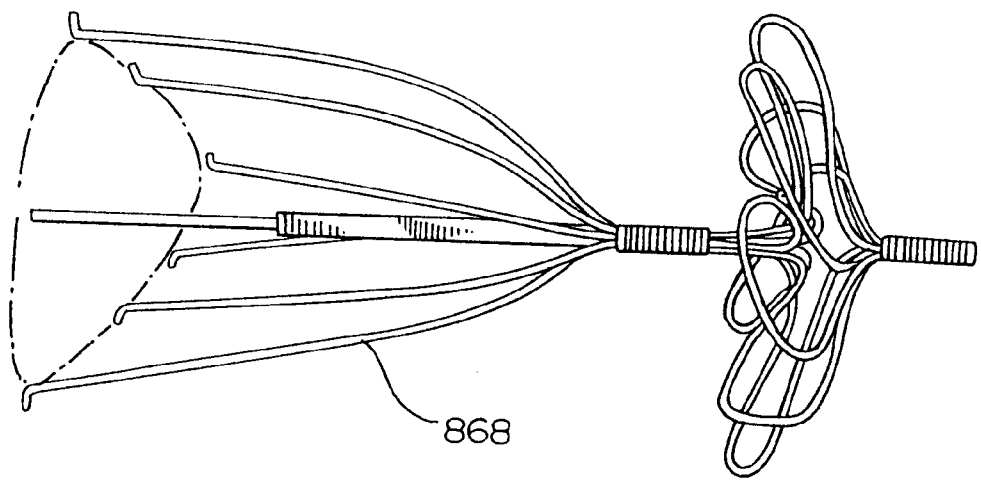
FIG. 8 shows a side elevational view of a vena cava filter for use with the inventive medical device delivery system.

Although the medical device shown in the figures have all been described as self-expanding stents, other mechanically expandable stents may be used as well, including balloon expandable stents. A perspective view of one suitable stent is shown in FIG. 6 at 668. Other medical devices suitable for delivery with the present delivery system include implants such as grafts and vena cava filters. A suitable graft is shown in FIG. 7 at 768 while a suitable vena cava filter is shown in FIG. 8 at 868.

As shown in the figures, the medical device delivery systems may further comprise other optional features, as are known in the art, such as bumpers 172, 272, 372 and 472 and markers 176, 276, 376 and 476. Bumpers 172–472 may be made of polyethylene and are affixed to inner tube 124 by adhesive such as H.B. Fuller 3507. Marker bands 176–476 are preferably made of a radio-opaque material such as gold although other materials such as stainless steel may be used as well. The markers are included to aid in positioning and may be affixed to inner tube 124 by adhesive such as Loctite 4011.

While several specific embodiments of the present invention have been described, the invention is directed more generally toward the inclusion of two sheaths in any other suitable catheter design not specifically described herein including fixed wire, over-the-wire and rapid-exchange catheters.

In the case of the fixed-wire design, the guidewire is fixedly attached to the medical device delivery system. A fixed-wire delivery system is described in U.S. Pat. No. 5,702,364 to Euteneuer et al., incorporated herein in its entirety by reference, and may be suitably modified for use with the inventive medical device delivery system.

In an over-the-wire embodiment, the inner tube extends proximally to a manifold and a guide wire may be inserted into the inner tube from the proximal end, the guide wire extending to the distal end of the system. The medical device delivery system may then ride on the guidewire.

Similarly, a rapid exchange delivery system is described in U.S. Pat. No. 5,534,007 to St. Germain et al., incorporated herein in its entirety by reference, and may be suitably modified for use with the inventive medical device delivery system. Specifically, the rapid-exchange version may be realized by terminating the inner tube in a guide wire port in a location along the system distal to the proximal end of the system to allow for insertion of a guide wire therein. In the rapid-exchange embodiment, only a portion of the medical device delivery system rides on a guidewire. Typically, the usable length of the medical device delivery system is approximately 135 cm. For a rapid-exchange medical device delivery system, the distance from where the guide wire accesses the inner tube to the distal tip will be approximately 5 cm to 35 cm.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A medical device delivery system having a proximal end and a distal end comprising:

an inner tube having a distal region and a proximal region and a medical device region at the distal region for disposing a medical device thereabout;

a distal inner sheath disposed about at least a portion of the medical device region, an inner sheath retraction device extending from the distal inner sheath to the proximal end of the medical device delivery system;

a distal outer sheath disposed about at least a portion of the medical device region; and an outer sheath retraction device extending from the distal outer sheath to the proximal end of the medical device delivery system wherein the distal inner sheath is constructed to be less creep resistant than the distal outer sheath.

2. The medical device delivery system of claim 1 wherein the retraction device comprises a pull-collar with a pull wire attached thereto.

3. The medical device delivery system of claim 1 wherein at least one of the inner sheath and the outer sheath is made of a porous material.

4. The medical device delivery system of claim 1 further comprising a medical device selected from the group consisting of stents, grafts and vena cava filters, the medical device disposed about the medical device region.

5. The medical device delivery system of claim 4 wherein the medical device is a stent.

6. The medical device delivery system of claim 5 wherein the stent is self-expandable.

7. A medical device delivery system having a proximal end and a distal end comprising:

an inner tube having a distal region and a proximal region and a medical device region at the distal region for disposing a medical device thereabout;

a distal inner sheath disposed about at least a portion of the medical device region, an inner sheath retraction device extending from the distal inner sheath to the proximal end of the medical device delivery system;

a distal outer sheath disposed about at least a portion of the medical device region; and an outer sheath retraction device extending from the distal outer sheath to the proximal end of the medical device delivery system wherein the distal outer sheath is made of a thicker material than the distal inner sheath.

8. A medical device delivery system having a proximal end and a distal end comprising:
- an inner tube having a distal region and a proximal region and a medical device region at the distal region for disposing a medical device thereabout;
- a distal inner sheath disposed about at least a portion of the medical device region,
- an inner sheath retraction device extending from the distal inner sheath to the proximal end of the medical device delivery system;
- a distal outer sheath disposed about at least a portion of the medical device region; and
- an outer sheath retraction device extending from the distal outer sheath to the proximal end of the medical device delivery system wherein the distal inner sheath is a perforated tear away sheath.

9. A medical device delivery system having a proximal end and a distal end comprising:
- an inner tube having a distal region and a proximal region and a medical device region at the distal region for disposing a medical device thereabout;
- a distal inner sheath disposed about at least a portion of the medical device region,
- an inner sheath retraction device extending from the distal inner sheath to the proximal end of the medical device delivery system;
- a distal outer sheath disposed about at least a portion of the medical device region; and
- an outer sheath retraction device extending from the distal outer sheath to the proximal end of the medical device delivery system wherein the outer sheath retraction device comprises:
  - a proximal outer tube having a distal end;
  - a collapsible sheath having a proximal end and a distal end, the proximal end of the collapsible sheath extending from the distal end of proximal outer tube;
  - a distal outer tube having a proximal end and a distal end, the proximal end of the distal outer tube extending from the distal end of the collapsible sheath; and
  - a slidable pull wire extending proximally from the distal outer sheath,
  - whereby the distal end of the retraction device moves in a proximal direction on sliding the pull wire proximally.

10. A medical device delivery system having a proximal end and a distal end comprising:
- an inner tube having a distal region and a proximal region and a medical device region at the distal region for disposing a medical device thereabout;
- a distal inner sheath disposed about at least a portion of the medical device region,
- an inner sheath retraction device extending from the distal inner sheath to the proximal end of the medical device delivery system;
- a distal outer sheath disposed about at least a portion of the medical device region; and
- an outer sheath retraction device extending from the distal outer sheath to the proximal end of the medical device delivery system wherein the distal inner sheath has an inner surface facing the inner tube and an outer surface facing the distal outer sheath and the distal outer sheath has an inner surface facing the distal inner sheath and an outer surface facing outward and a lubricant is applied to at least a portion of at least one of the outer surface of the distal inner sheath or the inner surface of the distal outer sheath so as to reduce frictional forces between the distal inner sheath and the distal outer sheath.

11. A stent delivery system having a proximal end and a distal end comprising:
- an inner tube with a distal region and a proximal region and a stent disposal region at the distal region for disposing a stent thereabout;
- a distal inner sheath disposed about the inner tube and covering the stent disposal region;
- an inner sheath retraction device having a distal end and a proximal end, the inner sheath retraction device extending proximally from the distal inner sheath;
- a distal outer sheath at least a portion of the outer sheath disposed about the stent disposal region; and
- an outer sheath retraction device having a distal end and a proximal end, the outer sheath retraction device extending proximally from the distal outer sheath wherein the distal inner sheath is constructed to be less creep resistant than the distal outer sheath.

12. A stent delivery system having a proximal end and a distal end comprising:
- an inner tube with a distal region and a proximal region and a stent disposal region at the distal region for disposing a stent thereabout;
- a distal inner sheath disposed about the inner tube and covering the stent disposal region;
- an inner sheath retraction device having a distal end and a proximal end, the inner sheath retraction device extending proximally from the distal inner sheath;
- a distal outer sheath at least a portion of the outer sheath disposed about the stent disposal region; and
- an outer sheath retraction device having a distal end and a proximal end, the outer sheath retraction device extending proximally from the distal outer sheath wherein the distal outer sheath is made of a thicker material than the distal inner sheath.

13. The stent delivery system of claim 12 wherein the inner sheath retraction device comprises a pull-collar with a pull wire attached thereto.

14. The stent delivery system of claim 12 wherein at least one of the inner sheath and the outer sheath is made of a porous material.

15. The stent delivery system of claim 12 further comprising a stent disposed about the medical device region.

16. The stent delivery system of claim 5 wherein the stent is balloon expandable.

17. The stent delivery system of claimed wherein the stent is self-expandable.

18. A stent delivery system having a proximal end and a distal end comprising:
- an inner tube with a distal region and a proximal region and a stent disposal region at the distal region for disposing a stent thereabout;
- a distal inner sheath disposed about the inner tube and covering the stent disposal region;
- an inner sheath retraction device having a distal end and a proximal end, the inner sheath retraction device extending proximally from the distal inner sheath;
- a distal outer sheath at least a portion of the outer sheath disposed about the stent disposal region; and
- an outer sheath retraction device having a distal end and a proximal end, the outer sheath retraction device extending proximally from the distal outer sheath wherein the outer sheath retraction device comprises:
a proximal outer tube having a distal end;
a collapsible sheath having a proximal and a distal end, the proximal end of the collapsible sheath extending from the distal end of proximal outer tube;
a distal outer tube having proximal and distal ends, the proximal end of the distal outer tube extending from the distal end of the collapsible sheath; and
a slidable pull wire extending proximally from the distal outer sheath,
whereby the distal end of the retraction device moves in a proximal direction on sliding the pull wire proximally.

19. A stent delivery system having a proximal end and a distal end comprising:
an inner tube with a distal region and a proximal region and a stent disposal region at the distal region for disposing a stent thereabout;
a distal inner sheath disposed about the inner tube and covering the stent disposal region;
an inner sheath retraction device having a distal end and a proximal end, the inner sheath retraction device extending proximally from the distal inner sheath;
a distal outer sheath at least a portion of the outer sheath disposed about the stent disposal region; and
an outer sheath retraction device having a distal end and a proximal end, the outer sheath retraction device extending proximally from the distal outer sheath wherein the inner sheath has an inner surface facing the inner tube and an outer surface facing the distal outer sheath and the distal outer sheath has an inner surface facing the distal inner sheath and an outer surface facing outward and a lubricant is applied to at least a portion of at least one of the outer surface of the distal inner sheath or the inner surface of the distal outer sheath so as to reduce frictional forces between the distal inner sheath and the distal outer sheath.

20. A medical device delivery system having a proximal and a distal end comprising:
an inner tube with a distal region and a proximal region, the inner tube having a medical device region at the distal region for disposing a medical device thereabout;
a distal inner scored tear away sheath disposed about the inner tube and covering at least a portion of the medical device region; and
a distal outer sheath, disposed about the distal inner scored tear away sheath and
an outer sheath retraction device having a distal end and a proximal end, the outer sheath retraction device extending proximally from the distal outer sheath wherein the distal inner scored tear away sheath is constructed to be less creep resistant than the distal outer sheath.

21. The medical device delivery system of claim 20 wherein the distal outer sheath is constructed to be creep resistant.

22. The medical device delivery system of claim 20 wherein the retraction device comprises a pull-collar with a pull wire attached thereto.

23. The medical device delivery system of claim 20 wherein at least one of the distal inner scored tear away sheath and the distal outer sheath is made of porous material.

24. The medical device delivery system of claim 20 further comprising a medical device selected from the group consisting of stents, grafts and vena cava filters, the medical device disposed about the medical device region.

25. The medical device delivery system of claim 24 wherein the medical device is a stent.

26. The medical device delivery system of claim 25 wherein the stent is self-expandable.

27. A medical device delivery system having a proximal and a distal end comprising:
an inner tube with a distal region and a proximal region, the inner tube having a medical device region at the distal region for disposing a medical device thereabout;
a distal inner scored tear away sheath disposed about the inner tube and covering at least a portion of the medical device region; and
a distal outer sheath, disposed about the distal inner scored tear away sheath and
an outer sheath retraction device having a distal end and a proximal end, the outer sheath retraction device extending proximally from the distal outer sheath wherein the distal outer sheath is made of a thicker material than the distal inner scored tear away sheath.

28. A medical device delivery system having a proximal and a distal end comprising:
an inner tube with a distal region and a proximal region, the inner tube having a medical device region at the distal region for disposing a medical device thereabout;
a distal inner scored tear away sheath disposed about the inner tube and covering at least a portion of the medical device region; and
a distal outer sheath, disposed about the distal inner scored tear away sheath and
an outer sheath retraction device having a distal end and a proximal end, the outer sheath retraction device extending proximally from the distal outer sheath wherein the distal inner scored tear away sheath has an inner surface facing the inner tube and an outer surface facing the distal outer sheath and the distal outer sheath has an inner surface facing the distal inner scored tear away sheath and an outer surface facing outward and a lubricant is applied to at least a portion of at least one of the outer surface of the distal inner scored tear away sheath or the inner surface of the distal outer sheath so as to reduce frictional forces between the distal outer sheath and the distal inner scored tear away sheath.

29. In a stent delivery system comprising a first retractable sheath carried over a stent, the first retractable sheath having an associated retraction device, the improvement being a second retractable sheath carried over the first retractable sheath, the second retractable sheath having an associated retraction device, the first retractable sheath constructed to be less creep resistant than the second retractable sheath.

* * * * *